United States Patent
Spohn et al.

(10) Patent No.: US 6,663,595 B2
(45) Date of Patent: Dec. 16, 2003

(54) PEELABLE PTFE SHEATHS AND METHODS FOR MANUFACTURE OF SAME

(75) Inventors: Peter Dwight Spohn, Brookline, NH (US); Dean David Dinsmore, New Ipswich, NH (US)

(73) Assignee: TFX Medical, Inc., Jaffrey, NH (US)

( * ) Notice: Subject to any disclaimer, the term of this patent is extended or adjusted under 35 U.S.C. 154(b) by 6 days.

(21) Appl. No.: 10/153,435

(22) Filed: May 21, 2002

(65) Prior Publication Data

US 2003/0088264 A1 May 8, 2003

Related U.S. Application Data

(62) Division of application No. 09/470,693, filed on Dec. 23, 1999, now Pat. No. 6,454,744.

(51) Int. Cl.[7] .............................................. A61M 5/178
(52) U.S. Cl. ................. 604/161; 604/164.05; 604/158; 604/164.01
(58) Field of Search ......................... 604/158, 160–161, 604/164.01–164.07, 165.01–165.03, 243, 264, 272; 264/632, 634, 638, 653, 662, 666, 514

(56) References Cited

U.S. PATENT DOCUMENTS

| | | | |
|---|---|---|---|
| 3,861,972 A | 1/1975 | Glover et al. |
| 4,306,562 A | 12/1981 | Osborne |
| 4,473,067 A | 9/1984 | Schiff |
| 4,753,765 A | 6/1988 | Pande |
| 5,180,372 A | 1/1993 | Vegoe et al. |

*Primary Examiner*—Michael J. Hayes
*Assistant Examiner*—Catherine Serke
(74) *Attorney, Agent, or Firm*—Edwards & Angell, LLP.; Peter F. Coreless; Christine C. O'Day

(57) ABSTRACT

The present invention provides improved medical introducer devices which incorporate a single or multi-layer PTFE peelable sheath. Devices of the present invention are suitable for use in inserting an ancilliary medical device, e.g., a catheter, guide wire and the like, into a patient. Methods of the present invention also are disclosed which employ a precision sintering process in order to produce sheaths having excellent tear properties and optimal peelability.

9 Claims, 2 Drawing Sheets

PEELABLE PTFE SHEATHS AND METHODS FOR MANUFACTURE OF SAME

This is a divisional of application Ser. No. 09/470,693, filed Dec. 23, 1999, now U.S. Pat. No. 6,454,744.

BACKGROUND OF THE INVENTION

1. Field of the Invention

The present invention relates to single and multi-layer polytetrafluoroethylene (PTFE) peelable sheaths and methods for manufacturing and use of such sheaths. Sheaths of the present invention are particularly suited for use as cannulas and other medical introducer devices.

2. Background

Splittable cannulas have been employed in various medical and surgical procedures for inserting catheters, guide wires and the like into patients. A typical procedure provides for insertion of a dilator or needle into the vasculature of a patient while encased within a splittable sheath. After insertion, the dilator or needle may be removed leaving the sheath protruding from the patient's vein. An ancillary medical device, e.g., a diagnostic or therapeutic catheter or guidewire, is then threaded through the sheath into the patient. The encasing sheath is then longitudinally sheared and removed from the catheter or guide wire and the patient such as by applying opposing force to opposed wings or tabs of the introducer device. See e.g., U.S. Pat. Nos. 5,334,157; 5,221,263; 5,141,497; 5,098,392; 4,772,266; and 4,243,050; and WO 97/14456 and WO 97/14468.

For ease in shearing and overall handling of the device, it is desirable to employ a sheath of minimal thickness, e.g., thin-walled, having some degree of flexibility.

Notable disadvantages have been observed when using devices which incorporate a "tear-away" or splittable sheath. For example, easy and non-traumatic removal of the sheath is critical. It is possible that the sheath may not tear evenly or completely, thereby necessitating additional maneuvering and application of excessive force to the device. Excessive movement or force exerted upon the sheath is likely to cause damage to the vasculature of the patient. There is also the potential of accidentally dislodging the catheter from its inserted position while trying to remove the sheath.

Many design configurations and processes have been investigated in an effort to overcome the various deficiencies observed in devices of the prior art which incorporate a peelable sheath.

For example, certain devices and methods were developed which employed a skiving process in order to produce peelable sheaths. Using such a process, approximately one half of the wall thickness of the tubing material, e.g. a plastic, typically is cut away in a longitudinal direction. In that way, a weak spot in the tubing wall is presented where the tubing material can be peeled.

U.S. Pat. No. 4,306,562 (Cook) discloses a flexible, tear apart cannula which may be removed by pulling tabs on opposite sides of the cannula following insertion of a catheter or other device into the body. That patent reports that the cannula tears readily in a longitudinal direction along the length of the structure because it comprises material having a longitudinal orientation, e.g., polytetrafluoroethylene or other plastics. The longitudinal orientation is achieved using a standard extrusion process, and a slitting operation is used to create the tabs for pulling the cannula apart. See also U.S. Pat. No. 4,581,025 (Cook).

It has been shown, however, that the cannulas produced in accordance with the Cook patents present certain limitations. For example, despite the fact that the tubing material has a longitudinal orientation, peelability still can be problematic. Additionally, certain additives which are added to the preferred tubing material, TEFLON (TEFLON is a registered trademark of DuPont for polytetrafluoroethylene), for X-ray visualization cause discoloration when the sheath is tipped by conventional thermal processes. Thus, the Cook devices may only be produced in dark colors (e.g., gray and black) that hide such discoloration.

U.S. Pat. No. 5,318,542 describes another process for producing a split cannula device having predetermined break lines which reportedly provides enhanced disassembly of the cannula. Predetermined break lines are produced by a non-metal-cutting shaping process, thereby enhancing uniformity of the predetermined break lines and reducing the force needed to disassemble the cannula. See also, U.S. Pat. No. 5,104,388.

SUMMARY OF THE INVENTION

There remains a need for improved medical introducer devices which incorporate a peelable sheath to facilitate smooth entry of an ancillary medical device into a patient, and easy and non-traumatic removal of the sheath following insertion of the ancilliary medical device.

It would be desirable to develop a multi-layer sheath configuration, e.g., an inner layer which permits visualization by X-ray or fluoroscopic procedures, and an outer layer that is resistant to discoloration by thermal processes. Such a configuration would be desirable in that the device could be produced in a variety of colors including white, blue or any other thermally stable color.

It also would be highly desirable to develop methods for the manufacture which produce single and multi-layer peelable sheaths with superior tear properties. More specifically, it would be highly desirable to develop methods for the manufacture of such sheaths which do not rely on mechanical skiving of the sheaths. We have found that skiving does not always produce tubing with good peel properties, especially when using tubing materials such as polytetrafluoroethylene.

We have now produced medical introducer devices which incorporate a single or multi-layer polytetrafluoroethylene-peelable (PTFE) sheath.

Preferred sheaths of the invention are characterized in part by being readily splittable along their length (longitudinally) without use of any type of mechanical skiving, score lines or the like.

The invention is based in part on the discovery that by imparting an appropriate longitudinal peel strength to a PTFE sheath, the sheath can be readily split as desired without the need for any type of mechanical skiving along the sheath length. Preferred peel strengths to provide such longitudinal splitting are disclosed below.

An appropriate peel strength is suitably imparted to a sheath by a controlled curing process, sometimes referred to herein as "precision sintering". Thus, temperature and cure times are selected to provide the appropriate peel strength. Optimal temperature and cure conditions will vary among specific cure systems. That is, cure conditions may vary with the type of heat source (e.g. radiant or convective heating), residence or exposure times of the PTFE sheath material to the heat source(s), size (e.g. French) of the sheath material being cured, and the like. See the examples which follow for exemplary suitable cure conditions for the described systems. Suitable cure conditions for any particular heating system and sheath material also can be readily determined empirically, i.e. a sheath material can be exposed to alternative cure conditions until conditions are identified that provide a desired peel strength. In other words, cure conditions can be applied, and the peel strength of the cured strength measured to determine if those conditions did in fact provide a targeted peel strength value. If the peel strength is not appropriate, the cure conditions are simply varied until a desired peel strength is provided.

Sheaths of the invention are useful for medical device applications, particularly for use in inserting an ancilliary medical device, e.g., a catheter, guide wire and the like, into a patient.

PTFE sheaths of the invention suitably may be of single layer or multiple layer constructions.

Preferred multi-layer devices afford significant advantages over the devices of the prior art. In one preferred multi-layer sheath of the invention, the outer layer comprises a thermally stable, colored pigment while at least one of the inner layers of the sheath comprises a detectable component, e.g. a radiopaque material for external visualization by X-ray or fluoroscopic procedures.

Using such a multi-layer configuration, no discoloration of the sheath is observed following conventional thermal tipping processes. Thus, devices of the present invention may be produced in a variety of colors, e.g., white, blue or any other thermally stable color, without sacrificing the radiopaque feature of the device.

The present invention also provides methods for manufacturing single or multi-layer peelable sheaths for use as cannulas and other medical introducer devices. Methods of the present invention incorporate extrusion followed by a precision sintering process as generally discussed above in order to achieve optimally cured tubing for use as a peelable sheath. Thus, there is no need to mechanically skive the wall of the tubing to present a weakened, predetermined break line.

Preferred methods for single layer sheath manufacture include: providing a preform PTFE material; extruding the PTFE material into tubing using conventional extrusion procedures; drying the tubing; and imparting a desired peel strength to the sheath that enables facile longitudinal splitting of the sheath without any type of mechanical skiving of the sheath. Precision sintering cure conditions are suitably employed to impart a desired peel strength. A detectable material may be added to the preform PTFE material in an amount sufficient to facilitate external visualization. Preferably, the detectable material comprises a radiopaque material for visualization by X-ray or fluoroscopic procedures.

Preferred methods for multiple layer sheath manufacture include the following: providing a first PTFE material blend for forming the inner layer of the sheath; preparing a second PTFE material for forming the outer layer of the sheath; combining the first and second PTFE materials blends into a two layer preform; extruding the two layer preform into tubing using conventional extrusion procedures; drying the tubing; and imparting a desired peel strength to the sheath that enables facile longitudinal splitting of the sheath without any type of mechanical skiving of the sheath. Precision sintering cure conditions are suitably employed to impart a desired peel strength.

A number of inner layer preform materials may be provided depending upon the number of inner layers desired, i.e. the multiple layer sheath may have 2 or more layers, typically 2, 3, 4 or 5 total layers. Again, a detectable material may be added to one of the preform materials in an amount sufficient to facilitate external visualization. Preferably, the detectable material comprises a radiopaque material for visualization by X-ray or fluoroscopic procedures.

Additionally, different colored pigments may be added to each of the outer and inner layer preform blends. In that way, though inseparable, the layers may be visibly distinguished.

A hub unit is preferably attached to either the single layer or multiple layer sheath on the sheath proximal end to facilitates splitting of the sheath upon application of an effective shearing force thereon. For example, preferred hub may have opposed outwardly extending "wing" portions that can be manipulated (e.g. downward or inward pressure) to facilitate longitudinal splitting of the sheath.

The sheath is also preferably tipped at the distal end thereof, e.g., using conventional thermal tipping processes.

Methods of introducing an ancilliary medical device, e.g., catheter or guidewire, using a device of the present invention generally include: inserting a needle or dilator assembly into the bore of a peelable sheath constructed in accordance with the present invention; piercing and dilating the vasculature of the patient using such an assembly; withdrawing the needle or dilator assembly from the sheath component of the device; inserting the catheter or guide wire through the bore of the sheath to the desired target location; applying outwardly cooperating forces to the hub unit, e.g., via attached wing portions, to axially shear the sheath; and removing the sheath from the vasculature of the patient.

Using methods of the present invention, single or multi-layer peelable sheaths are provided that facilitate easy, non-traumatic removal of the sheath following insertion of the ancilliary medical device.

Other aspects of the invention are discussed infra.

DETAILED DESCRIPTION

As discussed above, the present invention provides single and multi-layer peelable sheaths for use in medical devices such as cannulas and other introducer devices. Introducer devices are routinely used in a variety of medical and surgical applications, e.g., for insertion of an ancilliary medical device such as a catheter, guide wire into a patient. The present invention employs a precision sintering process in order to produce sheaths having excellent tear properties and optimal peelability.

Preferred sheaths of the invention will exhibit a peel strength of at least about 0.6 lbs., more preferably at least about 0.70 lbs., still more preferably at least about 0.80 lbs., 1.0 lbs., 1.2 lbs., 1.4 lbs., 1.6 lbs., 1.8 lbs. or 2.0 lbs., with a maximum peel strength of about 2.8 or 3.0 lbs.

Further preferred is where the sheath exhibits a relatively narrow standard deviation around a tested peel strength, such a standard deviation of no more than about ±0.40 lbs of a specific value, more preferably a standard deviation of no more than about ±0.30 lbs, 0.20 lbs or 0.10 lbs of a specific tested value.

As discussed above, preferred peel strengths will vary with sheath size, with generally higher peel strengths preferred for larger sheaths. More particularly, for a sheath having a size up to about 9 French (typically about 2, 3, or 4 French up to about 8 or 8.5 French), preferred peel strengths will be from about 0.5 lbs. up to about 2.0 lbs., more preferably 0.6 lbs to about 2.0 lbs. For a sheath having a size from about 9 to about 13 French, preferred peel strengths will be from about 0.75 lbs. up to about 2.5 lbs., more preferably 1.0 lbs to about 2.0 lbs. For a sheath having a size from about 14 to about 18 French or greater, preferred peel strengths will be from about 1.0 lbs. up to about 3.0 lbs., more preferably 1.0 lbs to about 2.5 lbs.

Figure 1:
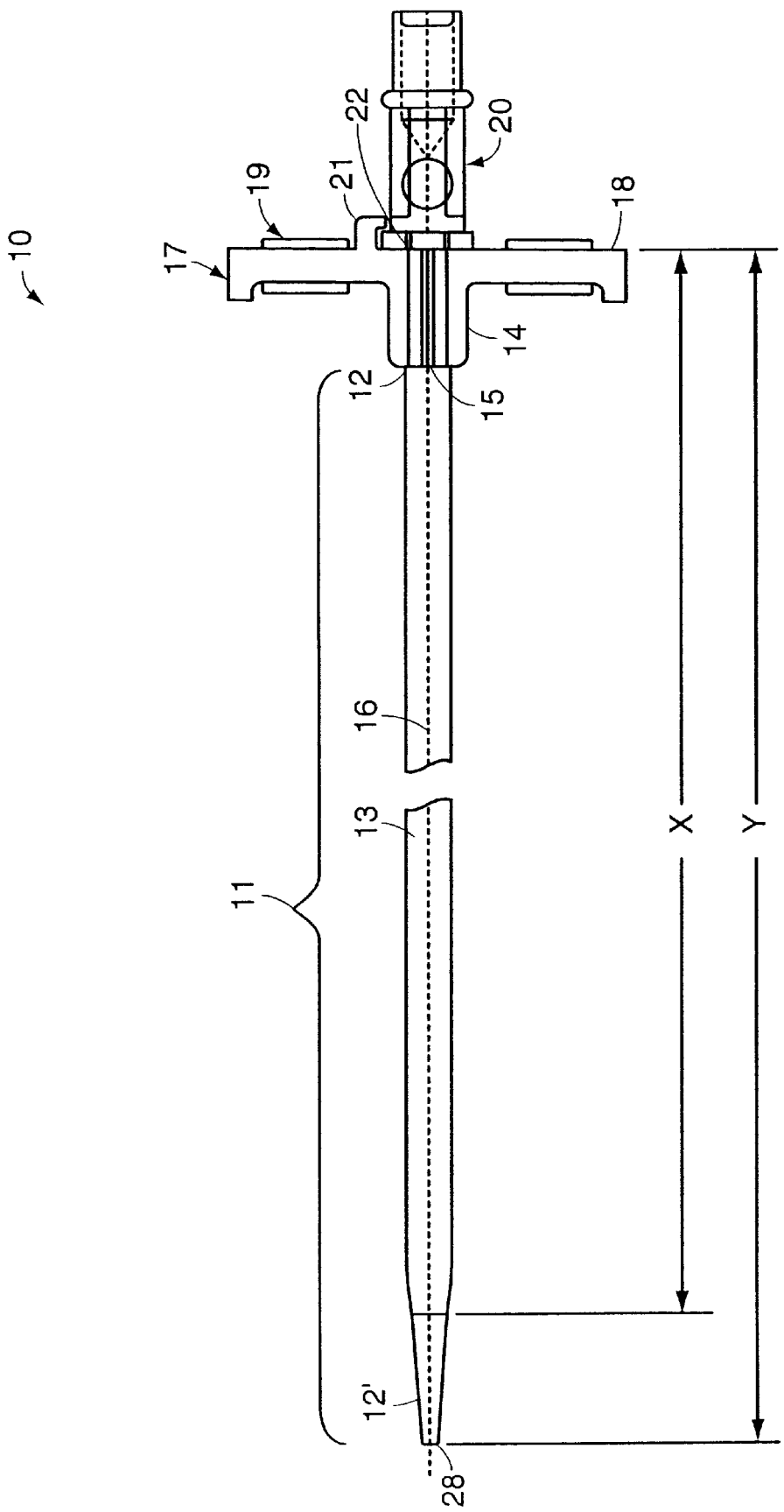
FIG. 1 is a side view of a medical introducer device which incorporates a single layer peelable sheath in a preferred embodiment of the present invention.

Referring now to the Drawings, FIG. 1 shows a preferred embodiment of a medical introducer device 10 constructed in accordance with the methods of the present invention. Device 10 comprises a single layer, peelable sheath 11 having a proximal end 12 and a tapered distal end 12', and a bore 13 extending therebetween. (In accordance with conventional practice, "proximal end" designates herein the specified end closest to the medical personnel manipulating the introducer device, and "distal end" designates the specified end closest to the patient.)

Sheath 11 is formed from a polytetrafluoroethylene polymer (e.g., TEFLON, registered trademark for polytetrafluoroethylene, commercially available from DuPont). Sheath 11 may further comprise materials such as fillers, colorants, and the like. Typical additional additives to the PTFE will be inorganic materials. It also will be possible, although typically less preferred, to include additional organic materials, particularly high Tg polymers, with the PTFE.

As discussed above, sheath 11 preferably further comprises a detectable material, e.g., a radiopaque material, in an amount sufficient for external visualization by X-ray or fluoroscopic procedures. Preferred radiopaque materials include barium sulfate, tungsten, bismuth sub-carbonate and bismuth trioxide. Preferably, the amount of radiopaque material present in the inner layer ranges from about 1% or 2% to about 12% by weight. Such a configuration permits visualization of the sheath within a patient by X-ray or fluoroscopic procedures.

Figure 2:
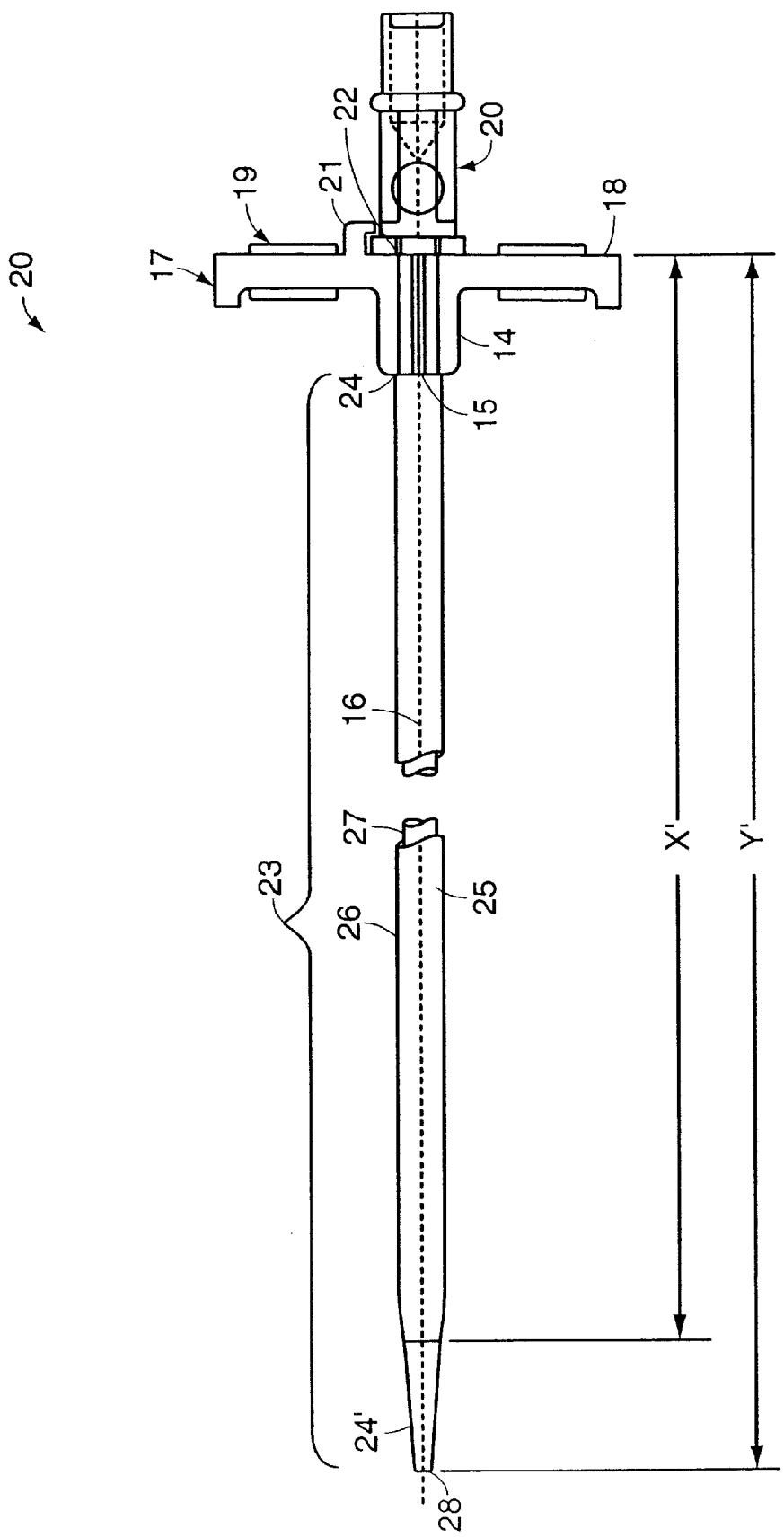
FIG. 2 is a side view of a medical introducer device which incorporates a multi-layer peelable sheath in an alternate preferred embodiment of the present invention.

Referring now to FIG. 2, an alternate embodiment of a medical introducer device of the present invention is shown. Device 20, constructed in accordance with the methods of the present invention, is shown to include a multi-layer, peelable sheath 23 having a proximal end 24 and a tapered distal end 24', and a bore 25 extending therebetween.

Sheath 23 preferably includes a thermally stable outer layer 26 and at least one inner layer 27. Preferably, both of these layers are formed from a flexible polymeric material, preferably a polytetrafluoroethylene polymer (e.g., TEFLON, registered trademark for polytetrafluoroethylene, commercially available from DuPont).

In preferred embodiments of the present invention, outer layer 26 further comprises a pigment that is not discolored by thermal processes.

In preferred embodiments of the present invention, inner layer 27 further comprises a detectable material, e.g., a radiopaque material, in an amount sufficient for external visualization by X-ray or fluoroscopic procedures. Preferred radiopaque materials include barium sulfate, tungsten, bismuth sub-carbonate and bismuth trioxide. Preferably, the amount of radiopaque material present in the inner layer ranges from about 1 or 2% to about 12% by weight. Such a configuration permits visualization of the sheath within a patient by X-ray or fluoroscopic procedures.

In particularly preferred embodiments, inner layer 27 additionally comprises a pigment (e.g., different in color from that of the outer layer) for visual distinction from outer layer 26.

Referring now to both FIGS. 1 and 2, devices of the present invention preferably further comprise a hub unit 14 attached, e.g., molded, to the sheath at a proximal end thereof. The hub unit 14 is capable of splitting the sheath upon application of an effective shearing force thereon.

Preferably, hub unit 14 is formed of polypropylene or other suitable material. In preferred embodiments, hub unit 14 substantially circumscribes the proximal end of the respective sheath and comprises a longitudinal score or indentation 15 on opposing sides. In that way, the hub is in contact with a significant circumferential surface area at the proximal end of the respective sheaths and a defined break line is presented for easy tearing of the sheath, e.g., along a longitudinal area 16. Using such a configuration, the potential for the sheath to tear unevenly or incompletely is avoided or at least significantly reduced.

In preferred embodiments of the present invention, two or more wing portions 17 and 18 are attached, e.g., molded to the hub unit 14. Wing portions 17 and 18 preferably extend outwardly from the hub unit in substantially diametrically opposed positions. Wing portions 17 and 18 facilitate easy grasping with respect to hub unit 14 and effective shearing of sheath 11 and sheath 23.

It also is particularly preferred that the outer surfaces of wing portions 17 and 18 include topography to aid in manipulation and overall handling of the introducer device. For example, as shown in the illustrative embodiments of FIGS. 1 and 2, preferably the exposed sides of wing portions 17 and 18 have a plurality of raised gripping surfaces 19.

In particularly preferred embodiments of the present invention, raised gripping surfaces 19 or other area(s) of wing portions 17 and 18 are color-coded to designate particular sheath dimensions. This feature enables easy identification by attendant medical personnel of a desired sheath size.

Sheaths 11 and 23 are typically adapted to snugly receive a conventional dilator assembly 20 or alternately, a needle assembly (not shown) in order to facilitate entry into a vein or artery of a patient.

Accordingly, in preferred embodiments of the present invention, wing portion 17 further comprises a locking lip 21 which secures flange 22 of dilator assembly 20 or a comparable flange of a needle assembly.

Generally, distal end 28 of dilator assembly 20 extends beyond the tapered distal end of the sheath in order to minimize trauma to the vasculature of the patient during the procedure.

Preferably, dilator assembly 20 is formed from a fluorinated ethylene-propylene resin. Other preferred fluorinated resins include, e.g., a tetrafluoroethylene polymer such as TEFLON (registered trademark of DuPont for polytetrafluoroethylene).

Following dilation of the vasculature of the patient, dilator assembly 20 is withdrawn and replaced with the desired ancilliary medical device, e.g. catheter or guidewire. Upon application of force to the hub unit 14 via wing portions 17 and 18, the sheath is peeled along longitudinal tear line 16 leaving only the ancilliary medical device in place within the vasculature of the patient.

Suitable dimensions of the components of devices of the present invention can vary rather widely depending on the intended application and such dimensions can be readily determined by those skilled in the art based on the present disclosure.

Generally, dilator assembly 20 (or, alternatively, a needle assembly) should have a diameter suitable for insertion into the selected vasculature of a patient. Sheath 11 and sheath 23 should have a diameter sufficient to accommodate such an assembly, and subsequently a catheter, guide wire or the like. Also, the diameters of the dilator as well as the sheath for circumscribing the dilator will be greater than the corresponding diameters of a device that employs a percutaneous needle rather than a dilator assembly.

For example, in particularly preferred embodiments of the present invention, peelable sheath 11 is about 5 to about 6 inches in length, denoted as x in FIG. 1. Preferably, dilator assembly 20 has a useable length (length excluding luer threads or other connector at proximal end 28) from about 7 inches to about 8 inches, denoted as y in FIG. 1.

Comparable dimensions, denoted by x' and y' in FIG. 2, are suitably preferred for the multi-layer embodiment 20.

Other preferred dimensions for devices of the present invention are shown in Table 1 below.

TABLE 1

| | DILATOR | | SHEATH | | |
|---|---|---|---|---|---|
| | | TIP I.D. MIN. | | | |
| FRENCH SIZE | O.D. AVG. (%/& .001) | (+.002/ −.000) | O.D. AVG. (%/& .001) | I.D. MIN | WALL |
| 4 F | .052 | .027 | .076 | .054 | .008/.009 |
| 5 F | .066 | .037 | .090 | .068 | .008/.009 |
| 6 F | .079 | .037 | .103 | .081 | .008/.009 |
| 7 F | .092 | .040 | .118 | .094 | .009/.010 |
| 8 F | .105 | .040 | .131 | .107 | 009/.010 |
| 9 F | .118 | .040 | .144 | .120 | .009/.010 |
| 10 F | .131 | .040 | .159 | .133 | .010/.011 |
| 10.5 F | .137 | .040 | .165 | .139 | .010/.011 |
| 11 F | .144 | .040 | .172 | .146 | .010/.011 |
| 12 F | .157 | .040 | .185 | .159 | .010/.011 |
| 12.5 F | .162 | .040 | .192 | .164 | .011/.012 |
| 13 F | .170 | .040 | .200 | .172 | .011/.012 |
| 14 F | .184 | .040 | .214 | .186 | .011/.012 |
| 15 F | .196 | .040 | .227 | .198 | .011/.012 |
| 16 F | .210 | .040 | .240 | .212 | .011/.012 |
| 18 F | .236 | .040 | .266 | .238 | .011/.012 |

The present invention also provides methods of manufacturing single or multi-layer peelable sheaths for use in medical devices such as cannulas and other introducer devices, e.g., sheaths for insertion of a catheter, guide wire and the like into a patient. Methods of the present invention incorporate extrusion followed by a precision sintering process in order to achieve optimally cured tubing for use as a peelable sheath. Thus, there is no need to mechanically skive the wall of the tubing to present a weakened, predetermined break line.

In the case of the multi-layer peelable sheath, methods of the present invention preferably also comprise adding different colored pigments to each of the outer and inner layer preform blends. Generally, such pigments are added in amounts which are sufficient to produce the desired colors. In that way, though inseparable, the layers may be visibly distinguished.

The multi-layer configuration presents significant advantages with respect to the devices of the prior art. In particular, we have discovered that if the sheath consists of a co-extrusion (two or more layers), it is possible to make any color sheath and that there is no visible discoloration of the external layer after thermal tipping. Thus, there is no need for devices of the present invention to be limited to a narrow range of colors (e.g., to dark colors only). Further, the ability to produce sheaths in lighter colors has the added advantage of enabling one to visualize contaminants that may be present in the sheath.

Preferably, a hydrocarbon lubricant is added to the preform blends, and the preform blends are allowed to equilibrate for a period of several hours prior to their combination in the case of the multi-layer sheath or prior to extrusion in the case of the single layer sheath.

Sheaths of the present invention are produced using standard single or multi-layer polytetrafluoroethylene (PTFE) extrusion procedures. For example, the two layer PTFE extrusion process is typically used to make fuel tubes with carbon-filled PTFE on the inside and natural PTFE on the outside. In utilizing this process, the present invention presents an improvement in terms of thermal resistance and color integrity of tubing.

As noted above, curing of the tubing is performed using a precision sintering process, e.g., reduced sintering. We have discovered that reduced sintering provides single or multi-layer tubing with excellent tear properties and optimal peelability. In contrast to the prior art, using the methods of the present invention, no skiving of the tubing is necessary to produce a peelable sheath.

Using the precision sintering process, the tubing is run through a series of temperature adjusted sintering ovens in order to produce tubing which is not only cured to the desired degree but which also has optimal tear properties, e.g., tensile strength and elongation, as well as peel strength.

Typically, the peel strength and other properties of the tubing are manually monitored at various intervals during the reduced sintering process. Various temperature adjustments and sintering times may be employed in order to produce tubing having the desired properties. However, the tubing is cured only until the desired peel strength is obtained.

Optimal peel strength will vary with tubing size. Referring to Table 2 below, target peel values are shown for various tubing sizes.

TABLE 2

| FRENCH SIZE | PEEL VALUE | STANDARD DEVIATION |
|---|---|---|
| 4 F–8.5 F | 0.85 | +/−0.50 lbs. |
| 9 F–13 F | 1.25 | +/−0.50 lbs. |
| 14 F–18 F | 1.80 | +/−0.60 lbs. |

In preferred embodiments of the present invention, methods of manufacture further comprise attaching, e.g., molding, a hub unit onto the proximal end of the sheath which facilitates splitting of the sheath upon application of an effective shearing force thereon; attaching and a plurality of wing portions to opposing sides of the hub unit; and tipping the sheath at a distal end thereof, e.g., using conventional thermal tipping processes.

The present invention also provides methods of introducing an ancilliary medical device, e.g., catheter or guidewire, using a device of the present invention. Such methods generally include: inserting a needle or dilator assembly into a peelable sheath constructed in accordance with methods of the present invention; piercing and dilating the vasculature of the patient using such an assembly; withdrawing the needle or dilator assembly from the sheath component of the device; inserting the catheter or guide wire through the bore of the sheath to the desired target location; applying outwardly cooperating forces to the hub unit, e.g., via attached wing portions, to axially shear the sheath; and removing the sheath from the vasculature of the patient.

The following non-limiting examples are illustrative of the invention.

EXAMPLE 1.

25 lb. of PTFE fine powder (Teflon® 6C, DuPont) was mixed with 4.35 lb. of a hydrocarbon lubricant (Isopar® G, Exxon), 3.245 lb. of a radioopaque filler (67% Bi2O3 in Isopar G), 0.5 lb. of Gray pigment concentrate (67% gray pigment in Isopar G) and 0.25 lb. of black pigment concentrate (67% black pigment in Isopar (® G). (Final composition is 7.8% $Bi_2O_3$, 1.2% gray, 0.6% black, based on total solids) These ingredients were mixed in a Patterson-Kelly V-cone blender for 20 minutes. This mix was then allowed to age for several hours to equilibrate.

The blend was made into a preform (2.5" OD, 0.625" ID). The object of preforming is to compact the blends in size and to make a preform that can be inserted into an extrusion machine. The preform was placed into an extrusion machine and extruded into tubing using a die and mandril (0.2880"OD, 0.2650"ID). The tubing was run through a drying oven to remove the hydrocarbon lubricant. The tubing was then run through 3 sintering ovens to cure the material. This tubing was then cut into 8.25" lengths.

The tubing produced had dimensions of 0.240" OD×0.2170" ID×8.25" long. The wall thickness was 0.0115". The overall tube was black with a shiny surface.

Referring to Table 3 below, properties of the tubing produced in this example are shown below as "Sample 2". Data for Samples 1, 3 and 4 are shown for purposes of comparison.

TABLE 3

|  | SAMPLE 1 PRIOR ART SAMPLE | SAMPLE 2 PRESENT INVENTION | SAMPLE 3 UNDER-CURE | SAMPLE 4 OVERCURE |
|---|---|---|---|---|
| Drying oven 1 (F.) | 400 | 400 | 400 | 400 |
| Curing oven 1 (F.) | 840 | 720 | 700 | 1000 |
| Curing oven 2 (F.) | 940 | 820 | 800 | 1080 |
| Curing oven 3 (F.) | 1040 | 920 | 900 | 1180 |
| Melting Point (C.) | 326.63 | 326.57 | 343.77 | 326.03 |
| Width at Half Height (C.) | 4.0 | 6.0 | 5.6 | 3.3 |
| Tensile Strength (PSI) | 7083 | 6817 | 1333 | 5417 |
| Elongation (%) | 288 | 309 | 233 | 351 |
| Peel strength (lb) | 1.95 | 1.56 | 1.2 | 2.67 |
| Peel Comments | Uneven peel, partial peel | Straight, even peel | Straight, even peel. Lots of stringers. | Uneven peel, partial peel |

Description of Samples:

Sample 1—This sample is presented for purposes of comparison. It is a commercially available product comprising PTFE, and has a narrow melting point peak at 327 degrees C. When split and peeled, it requires higher peel force and does not peel smoothly. The tubing begins to peel and then one of the sections begins to narrow down and eventually ends before all of the tubing is split (partial peel).

Sample 2—This sample corresponds to a peelable product manufactured in accordance with the methods of present invention. This product is not fully cured as indicated by the wider melting point peak. The tensile strength and elongation are similar to the fully cured product. However, the peel strength is reduced by 20% in relation to the fully cured product. The peel is straight and even so that the entire tubing is split.

Sample 3—This sample corresponds to a product that is almost completely uncured. This is visible by a melting peak at 344 degrees C. versus 327 degrees C. for the other samples. This product is mottled white and black due to the undercure. The peel is straight and even, however, there are significant numbers of fibers that extend from the peeled surface after peeling. This is unacceptable to the end user since a piece may tear away and contaminate the area. In addition, the physical properties are significantly reduced due to the lack of curing of the product.

Sample 4—This sample corresponds to a product that is cured harder than normal. This overcure is visible by the melting peak half width. This product does not peel straight, similar to the fully cured product.

EXAMPLE 2.

Blend 1—55.1 lb. of PTFE fine powder (Teflon® 6C, DuPont) was mixed with 9.048 lb. of a hydrocarbon lubricant (Isopar®G, Exxon), and 7.151 lb. of a radiopaque filler (67% Bi2O3 in Isopar G) (final composition is 6.7% $Bi_2O_3$ based on total solids). These ingredients were mixed in a Patterson-Kelly V-cone blender for 20 minutes. This mix was then allowed to age for several hours to equilibrate.

Blend 2—55.1 lb. of PTFE fine powder (Teflon® 6C, DuPont) was mixed with 10.379 lb. of a hydrocarbon lubricant (Isopar® G, Exxon), and. 0.573 lb. of a white pigment filler (67% white pigment in Isopar G). These ingredients were mixed in a Patterson-Kelly V-cone blender for 20 minutes. This mix was then allowed to age for several hours to equilibrate.

The blends were made into a two layer preform (2.5" OD, 0.625" ID) with Blend 1 on the ID and Blend 2 on the OD. The object of preforming is to compact the blends in size and to make a preform that can be inserted into an extrusion machine. The preform was placed into an extrusion machine and extruded into tubing using a die and mandril. (0.2880"OD, 0.2650"ID) The tubing was run through a drying oven to remove the hydrocarbon lubricant. The tubing was then run through 3 sintering ovens to cure the material. This tubing was then cut into 8.25" lengths.

The tubing produced has dimensions of 0.240" OD×0.2170" ID×8.25" long. The wall thickness is 0.0115". The overall tube is two layers with a shiny white outside layer and a yellow inside layer.

TABLE 4

|  | SAMPLE 1 PRESENT INVENTION | SAMPLE 2 UNDER-CURE | SAMPLE 3 OVERCURE |
|---|---|---|---|
| Drying oven 1 (F.) | 400 | 400 | 400 |
| Curing oven 1 (F.) | 820 | 720 | 1000 |
| Curing oven 2 (F.) | 920 | 820 | 1160 |
| Curing oven 3 (F.) | 1000 | 920 | 1160 |
| Melting Point (C.) | 325.96 | 343.33 | 329.38 |
| Tensile Strength (PSI) | 7000 | 1333 | 7400 |
| Elongation (%) | 250 | 250 | 350 |
| Peel strength (lb) | 1.56 | 0.4 | >2.5* |
| Peel Comments | Straight, even peel | Straight, even peel. Lots of stringers. | *Could not peel. |

Description of Samples:

Sample 1—This is an example of the present invention. This is a peelable product. This product is precision sintered. The peel strength is typical for precision sintered product. The peel is straight and even so that the entire tubing is split.

Sample 2—This sample is almost completely uncured product. This is visible by a melting peak at 344 degrees C. versus 327 degrees C. for the other samples. This product is opaque, dull white due to the undercure. The peel is straight and even, however, there are significant numbers of fibers that stick out of the peeled surface after being peeled. The peel strength is unacceptably low. This is unacceptable to the end user since a piece may tear away and contaminate the area. In addition, the physical properties are significantly reduced due to the lack of curing of the product.

Sample 3—This product is fully cured. This makes a tube that is dimensionally stable, but cannot be peeled. The peel force increases to greater than 2.5 lb. and then the product tears. This product does not peel evenly.

EXAMPLE 3.

Tubing manufacturing: Blend 1—25 lb. of PTFE fine powder (Teflon® T6C, DuPont) was mixed with 4.5 lb. of a hydrocarbon lubricant (Isopar® G, Exxon) and 3.3 lb. of a radiopaque filler (67% $Bi_2O_3$ in Isopar G, Caloric) in a Patterson-Kelly V-cone blender. The materials were blended for 20 minutes. This mix was then allowed to age for several hours to equilibrate.

Blend 2—25 lb. of PTFE fine powder (Teflon® T6C, DuPont) was mixed with 5.1 lb. of a hydrocarbon lubricant (Isopar® G, Exxon) and 0.3 lb. of a white pigment (67% white pigment in Isopar G, Caloric) in a Patterson-Kelly V-cone blender. The materials were blended for 20 minutes. This mix was then allowed to age for several hours to equilibrate.

The two blends were then made into a two layer preform (2.5" OD, 0.625" ID) with Blend 2 on the OD and Blend 1 on the ID. (The object of preforming is to compact the blends in size and to make a preform that can be inserted into an extrusion machine.) The preform was placed into an extrusion machine and extruded into tubing. The tubing was run through a drying oven at approximately 400 degrees F. to remove the hydrocarbon lubricant. The tubing was then run through sintering ovens at approximately 1000 degrees F. to cure the material. This tubing was cut into 8.25" lengths.

The tubing produced had dimensions of 0.144" OD×0.125" ID×8.25" in length with a wall thickness of 0.0095". The outer 0.00475" was Blend 2 and the inner 0.00475" was Blend 1. The overall tube had a white color with a yellow inside when cut apart.

Device manufacture: The tubing was then punched with two holes. A slit was made between the two holes. Buttons were placed in the punched holes and a hub was overmolded onto the tubing. The opposite end was then tipped using a Rf tipping machine and trimmed to size. The finished sheath assembly was white in color with no visible discoloration. The sheath assembly was then placed over a matching size dilator.

EXAMPLE 4.

This example shows how additional heat added to a precision sintered product renders it useless for peelable PTFE. The table illustrates that precision sintered product can be taken out of the useful range by the application of additional heat. It also shows that skived product is not affected by the addition of additional heat.

TABLE 5

|  | SAMPLE 1 | SAMPLE 2 | SAMPLE 3 |
|---|---|---|---|
| Skived | No | No | Yes |
| Precision sintered | Yes | Yes | Yes |
| Post cured | No | Yes | Yes |
| Peel Strength (lb.) | 1.63 | 2.93 | 1.26 |
| Peel Comments | Straight, even peel | Uneven peel, partial peel | Straight even peel |

Description of Samples:

Sample 1—Product from Example 1, Sample 2.

Sample 2—Product from Example 1, Sample 2 was taken and placed in a 700 degree F. oven for 20 minutes. This product is no longer precision sintered since it was post-sintered.

Sample 3—Product from Example 1, Sample 2 that was skived and then placed in a 700 degree F. oven for 20 minutes. This product is no longer precision sintered since it was post-sintered.

Comparative Example 1.

The tubing was made identical to Example 3 except that instead of using Blend 2 on the OD, Blend 1 was used for the entire preform. Thus, one layer of tubing is produced that is Blend 1 throughout. This produced tubing that was yellow in color.

The tubing was finished in the same manner as listed in Example 3. The finished sheath assembly was yellow in color with brown and black colored spots in the tipped section. This is unacceptable for high quality product.

Comparative Example 2.

Blend 3 is a combination of Blend 1 and Blend 2—25 lb. of PTFE fine powder (Teflon® T6C, DuPont) was mixed with 4.4 lb. of a hydrocarbon lubricant (Isopar® G, Exxon), 3.3 lb. of a radiopaque filler (67% $Bi_2O_3$ in Isopar G, Caloric), and 0.3 lb. of a white pigment (67% white pigment in Isopar G, Caloric) in a Patterson-Kelly V-cone blender. The materials were blended for 20 minutes. This mix was then allowed to age for several hours to equilibrate.

The tubing was made identical as that described in Comparative Example 1 except that instead of using Blend 2, Blend 3 was used. This produced tubing that was white in color and radiopaque.

The tubing was finished in the same manner as described in Example 3. The finished sheath assembly was white in color with brown and black colored spots in the tipped section. This is unacceptable for high quality product.

The foregoing description of the present invention is merely illustrative thereof, and it is understood that variations and modification can be made without departing from the spirit or scope of the invention as set forth in the following examples and claims.

What is claimed is:

1. A medical introducer device comprising:

(a) a single-layer, peelable PTFE sheath having a bore extending therethrough and that does not include mechanically produced skiving for longitudinal splitting of the sheath, the sheath thermally cured to provide a peel strength of at least about 0.5 lbs with a standard deviation of no greater than about 0.40 lbs; and (b) a hub unit attached at a proximal end of the peelable sheath which facilitates splitting of the peelable sheath upon application of an effective shearing force thereon.

2. The device of claim 1 wherein the peel strength is at least about 0.70 lbs.

3. The device of claim 1 wherein the peel strength is at least about 1.0 lbs.

4. The device of claim 1 wherein the peel strength standard deviation is no more than about 0.30 lbs.

5. The device of claim 1 wherein the peel strength standard deviation is no more than about 0.20 lbs.

6. The device of claim 1 further comprising a plurality of wing portions attached to the hub unit on opposing sides for grasping the hub unit.

7. The device of claim 1 wherein the peelable sheath comprises a detectable material capable of external visualization.

8. The device of claim 1 further comprising a needle or dilator assembly extending longitudinally within the bore of the peelable sheath.

9. A method of introducing a catheter or guide wire into a patient comprising:

(a) providing a medical introducer device of claim 1;

(b) piercing and dilating the vasculature of the patient using the needle or dilator assembly;

(c) inserting the catheter or guidewire through the bore of the peelable sheath into vasculature of the patient;

(d) applying cooperating forces to the wing portions of the hub unit to axially shear the peelable sheath; and (e) removing the peelable sheath from the vasculature of the patient.

* * * * *